United States Patent
McGuigan et al.

(10) Patent No.: US 8,658,616 B2
(45) Date of Patent: Feb. 25, 2014

(54) NUCLEOSIDE ARYL PHOSPHORAMIDATES AND THEIR USE AS ANTI-VIRAL AGENTS FOR THE TREATMENT OF HEPATITIS C VIRUS

(75) Inventors: Christopher McGuigan, Cardiff (GB); Plinio Perrone, Cardiff (GB); Johan Neyts, Leuven (BE)

(73) Assignees: University College Cardiff Consultants Limited, Cardiff (GB); K.U. Leuven Research and Development, Leuven (BE)

( * ) Notice: Subject to any disclaimer, the term of this patent is extended or adjusted under 35 U.S.C. 154(b) by 582 days.

(21) Appl. No.: 12/516,253

(22) PCT Filed: Nov. 23, 2007

(86) PCT No.: PCT/GB2007/004480
§ 371 (c)(1),
(2), (4) Date: Jan. 24, 2011

(87) PCT Pub. No.: WO2008/062206
PCT Pub. Date: May 29, 2008

(65) Prior Publication Data
US 2011/0124592 A1     May 26, 2011

(30) Foreign Application Priority Data
Nov. 24, 2006  (GB) .................................. 0623493.4

(51) Int. Cl.
*A61K 31/70*  (2006.01)
*A01N 43/04*  (2006.01)
*C07H 19/167* (2006.01)
*C07H 19/173* (2006.01)

(52) U.S. Cl.
USPC ........... 514/47; 514/48; 536/27.6; 536/27.62; 536/27.63; 536/27.7; 536/27.81

(58) Field of Classification Search
None
See application file for complete search history.

(56) References Cited

U.S. PATENT DOCUMENTS

| | | | |
|---|---|---|---|
| 5,614,504 A | 3/1997 | Hadden | |
| 6,030,957 A | 2/2000 | Uckun | |
| 6,350,736 B1 | 2/2002 | Uckun | |
| 6,441,161 B1 | 8/2002 | Kirschenheuter et al. | |
| 6,455,513 B1 | 9/2002 | McGuigan | |
| 6,475,985 B1 | 11/2002 | Wagner et al. | |
| 6,596,700 B2 | 7/2003 | Sommadossi et al. | |
| 6,620,796 B1 | 9/2003 | Zhou et al. | |
| 7,018,989 B2 | 3/2006 | McGuigan et al. | |
| 7,101,861 B2 | 9/2006 | Sommadossi et al. | |
| 7,105,493 B2 | 9/2006 | Sommadossi et al. | |
| 7,144,874 B2 | 12/2006 | Uckun | |
| 7,148,206 B2 | 12/2006 | Sommadossi et al. | |
| 7,157,441 B2 | 1/2007 | Sommadossi et al. | |
| 7,169,766 B2 | 1/2007 | Sommadossi et al. | |
| 2002/0035085 A1 | 3/2002 | Sommadossi et al. | |
| 2003/0050229 A1 | 3/2003 | Sommadossi et al. | |
| 2003/0120071 A1 | 6/2003 | McGuigan et al. | |
| 2004/0087549 A1 | 5/2004 | Uckun et al. | |
| 2004/0097461 A1 | 5/2004 | Sommadossi et al. | |
| 2004/0101535 A1 | 5/2004 | Sommadossi et al. | |
| 2005/0009775 A1 | 1/2005 | Howes et al. | |
| 2005/0137161 A1 | 6/2005 | Sommadossi et al. | |
| 2006/0014943 A1 | 1/2006 | Dempcy et al. | |
| 2006/0142238 A1 | 6/2006 | McGuigan et al. | |
| 2006/0241064 A1 | 10/2006 | Roberts et al. | |

(Continued)

FOREIGN PATENT DOCUMENTS

| EP | 1 292 603 | 3/2003 |
|---|---|---|
| EP | 1 294 735 | 3/2003 |

(Continued)

OTHER PUBLICATIONS

McGuigan et al, "Application of Phosphoramidate ProTide Technology Significantly Improves Antiviral Potency of Carbocyclic Adenosine Derivatives", 2006, pp. 7215-7226, vol. 49, J. Med. Chem.

(Continued)

*Primary Examiner* — Lawrence E Crane
(74) *Attorney, Agent, or Firm* — B. Aaron Schulman; Stites & Harbison, PLLC

(57) ABSTRACT

Compounds having the general formula (I):

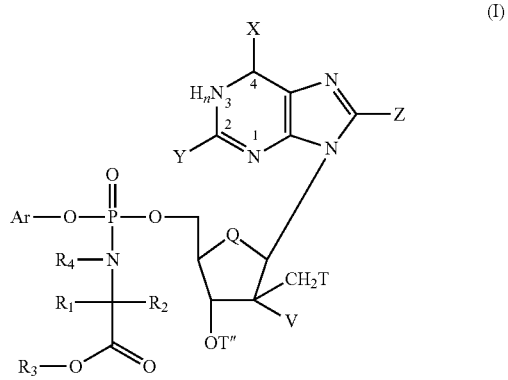

are provided which have enhanced inhibitory potency and are thus useful in methods of prophylaxis or treatment of a viral infection such as hepatitis C virus. The compounds are phosphoramidate derivatives of nucleoside compounds derived from bases such as adenine and guanine. The glycoside moiety of the nucleoside compound can be substituted at the ss-2' position with methyl and the phosphoramidate group can be 1-naphthyl linked by —O— to the P atom. These compounds can be administered as pharmaceutical compositions, and methods for their preparation are also provided.

22 Claims, No Drawings

(56) References Cited

U.S. PATENT DOCUMENTS

| | | |
|---|---|---|
| 2007/0042988 A1 | 2/2007 | Klumpp et al. |
| 2007/0060744 A1 | 3/2007 | Dempcy et al. |
| 2007/0265222 A1 | 11/2007 | MacCross et al. |
| 2008/0280842 A1 | 11/2008 | MacCross et al. |
| 2009/0215715 A1 | 8/2009 | McGuigan et al. |
| 2009/0306007 A1 | 12/2009 | Wagner et al. |
| 2010/0016251 A1 | 1/2010 | Sofia et al. |
| 2010/0022468 A1 | 1/2010 | Meppen et al. |
| 2010/0035835 A1 | 2/2010 | Narjes et al. |
| 2010/0234316 A1 | 9/2010 | Maccross et al. |

FOREIGN PATENT DOCUMENTS

| | | |
|---|---|---|
| EP | 1 669 364 | 6/2006 |
| EP | 1 736 478 | 12/2006 |
| WO | WO-96/33203 | 10/1996 |
| WO | WO-97/21452 | 6/1997 |
| WO | WO-02/28875 | 4/2002 |
| WO | WO-02/057287 | 7/2002 |
| WO | WO-02/057425 | 7/2002 |
| WO | WO-03/051899 | 6/2003 |
| WO | WO-03/061385 | 7/2003 |
| WO | WO-03/061576 | 7/2003 |
| WO | WO-03/062256 | 7/2003 |
| WO | WO-03/062257 | 7/2003 |
| WO | WO-2003/062255 | 7/2003 |
| WO | WO-03/063771 | 8/2003 |
| WO | WO-03/068162 | 8/2003 |
| WO | WO-2004/029277 | 4/2004 |
| WO | WO 2006/100439 | 9/2006 |
| WO | WO-2006/116557 | 11/2006 |
| WO | WO 2006/121820 | 11/2006 |
| WO | WO-2008/062206 | 5/2008 |
| WO | WO-2008/104408 | 9/2008 |

OTHER PUBLICATIONS

McGuigan et al, "Application of Phosphoramidate Pronucleotide Technology to Abacavir Leads to a Significant Enhancement of Antiviral Potency", 2005, pp. 3504-3515, vol. 48, J. Med. Chem.

Cahard et al, "Aryloxy Phosphoramidate Triesters as Pro-Tides", 2004, pp. 371-382, vol. 4, Mini-Reviews in Medicinal Chemistry.

Office Action in corresponding Japanese Application No. 2009-537699.

Venkatachalam, T.K. et al, "Synthesis and metabolism of naphthyl substituted phosphoramidate derivatives of stavudine", Aug. 1, 2006, pp. 5161-5177, vol. 14, No. 15, Bioorganic & Medicinal Chemistry.

Written Opinion and Search Report in corresponding Singapore Application No. 201102856-0 dated Apr. 12, 2013.

Tudor et al, "Enhanced inhibition of the EDHF phenomenon by a phenyl methoxyalaninyl phosphoramidate derivative of dideoxyadenosine", 2004, pp. 27-30, vol. 142, British Journal of Pharmacology.

NUCLEOSIDE ARYL PHOSPHORAMIDATES AND THEIR USE AS ANTI-VIRAL AGENTS FOR THE TREATMENT OF HEPATITIS C VIRUS

CROSS-REFERENCE TO RELATED APPLICATIONS

The present application is a 371 application based on PCT/GB2007/004480, filed Nov. 23, 2007.

The present invention relates to chemical compounds, their preparation and their use in the treatment and prophylaxis of viral infections, particularly in homo sapiens. Particularly, although not exclusively, the present invention relates to chemical compounds useful as anti-viral agents active with respect to hepatitis C virus (HCV).

WO 2006/012078 A describes certain nucleoside aryl phosphoramidates, their synthesis, and their use as precursors to inhibitors of RNA-dependent RNA viral polymerase, particularly their use as precursors to inhibitors of hepatitis C virus (HCV) NS5B polymerase, as precursors to inhibitors of HCV replication, and for the treatment of hepatitis C infection.

WO 2006/100439 A relates to phosphoramidates of cladribine, isocladribine, fludaribine and clofarbine and their use in the treatment of a cancer such as leukaemia.

The intracellular kinase-mediated activation of the compounds described in WO 2006/100439 A with respect to their treatment of cancer is different to the intracellular kinase-mediated activation required in the treatment and prophylaxis of viral infections.

It is an object of the present invention to provide novel chemical compounds that provide improved prophylaxis and treatment of viral infections in homo sapiens, in particular improved prophylaxis and treatment of hepatitis C infection in homo sapiens.

According to a first aspect of the present invention there is provided a compound of formula I:

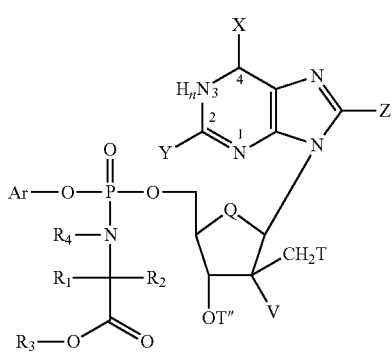

wherein:

Ar comprises two or more fused aromatic rings and is selected from the group consisting of $C_{9-30}$aryl and $C_{6-30}$heteroaryl, any of which rings are optionally substituted;

T is selected from the group consisting of hydrogen (—H), fluoro (—F), azido (—$N_3$), amino (—$NH_2$), hydroxy (—OH), $C_{1-3}$alkyl ($C_{1-3}$—), $C_{1-3}$alkoxy ($C_{1-3}$O—), mercapto (—SH) and $C_{1-3}$alkylthio ($C_{1-3}$S—);

V is selected from the group consisting of —OT', hydrogen (—H), fluoro (—F) and chloro (—Cl), where T' is selected from the group consisting of hydrogen (—H), methyl (—$CH_3$), $C_{1-16}$alkylcarbonyl ($C_{1-16}$alkyl-C(=O)—), $C_{2-18}$alkenylcarbonyl ($C_{2-18}$alkenyl-C(=O)—), $C_{1-10}$alkoxycarbonyl ($C_{1-10}$alkyl-O—C(=O)—), $C_{3-6}$cycloalkylcarbonyl ($C_{3-6}$cycloalkyl-C(=O)—) and $C_{3-6}$cycloalkyloxycarbonyl ($C_{3-6}$cycloalkyl-O—C(=O)—);

T" is selected from the group consisting of hydrogen (—H), methyl (—$CH_3$), $C_{1-16}$alkylcarbonyl ($C_{1-16}$alkyl-C(=O)—), $C_{2-18}$alkenylcarbonyl ($C_{2-18}$alkenyl-C(=O)—), $C_{1-10}$alkoxycarbonyl ($C_{1-10}$alkyl-O—C(=O)—), $C_{3-6}$cycloalkylcarbonyl ($C_{3-6}$cycloalkyl-C(=O)—) and $C_{3-6}$cycloalkyloxycarbonyl ($C_{3-6}$cycloalkyl-O—C(=O)—);

n is 0 or 1, wherein
when n is 1, X is =O, and
when n is 0, a double bond exists between position 3 and position 4 and X is selected from the group consisting of H, OH, F, Cl, Br, I, $C_{1-6}$alkyl and $NR_5R_6$, where each of $R_5$ and $R_6$ is independently selected from H and $C_{1-6}$alkyl;

Z is selected from the group consisting of H, OH, F, Cl, Br, I, $C_{1-6}$alkyl and $NR_5R_6$, where each of $R_5$ and $R_6$ is independently selected from H and $C_{1-6}$alkyl;

Y is selected from the group consisting of H, OH, F, Cl, Br, I, $C_{1-6}$alkyl, $C_{2-8}$alkynyl and $NR_5R_6$, where each of $R_5$ and $R_6$ is independently selected from H and $C_{1-6}$alkyl;

Q is selected from the group consisting of O, S and $CR_7R_8$, where $R_7$ and $R_8$ are independently selected from H and $C_{1-6}$alkyl;

each of $R_1$ and $R_2$ is independently selected from H, and the group consisting of $C_{1-20}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy, $C_{5-20}$heterocyclyl, any of which is optionally substituted; and each of $R_3$ and $R_4$ is independently selected from H, and the group consisting of $C_{1-20}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy, $C_{5-20}$heterocyclyl, any of which is optionally substituted, preferably $R_3$ is alkyl, more preferably $R_3$ is selected from the group consisting of methyl, ethyl, 2-propyl, n-propyl, cyclohexyl, 2-butyl and benzyl;

with the proviso that $R_1$ and $R_4$ can together comprise a —$(CH_2)_3$— alkylene chain;

and pharmaceutically acceptable salts, solvates and prodrugs thereof.

According to a further aspect of the present invention there is provided a compound of formula I for use in a method of treatment, suitably in the prophylaxis or treatment of a viral infection, more suitably in the prophylaxis or treatment of hepatitis C virus.

According to a further aspect of the present invention there is provided the use of a compound of formula I in the manufacture of a medicament for the prophylaxis or treatment of a viral infection, preferably a medicament for the prophylaxis or treatment of hepatitis C virus.

According to a further aspect of the present invention, there is provided a method of prophylaxis or treatment of a viral infection, particularly hepatitis C virus, comprising administration to a patient, suitably a homo sapiens, in need of such treatment an effective dose of a compound of formula I.

According to a further aspect of the present invention, there is provided a pharmaceutical composition comprising a compound of formula I in combination with a pharmaceutically acceptable carrier, diluent or excipient.

According to a further aspect of the present invention there is provided a method of preparing a pharmaceutical composition comprising the step of combining a compound of formula I with a pharmaceutically acceptable excipient, carrier or diluent.

According to a further aspect of the present invention there is provided a process for the preparation of a compound of formula I, the process comprising reacting a compound of formula III:

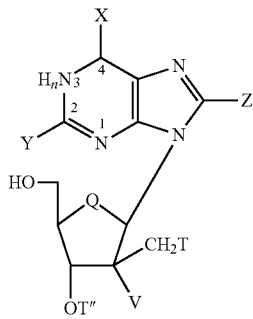

with a compound of formula IV:

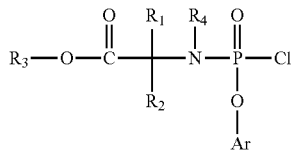

where Ar, T, V, T", n, X, Y, Z, Q, $R_1$, $R_2$, $R_3$ and $R_4$ have the meanings set out above with respect to Formula I.

It is to be understood that the present invention extends to metabolic intermediates of compounds of formula I, wherein Ar is H and $R_3$ is H or $R_3$ is as defined above.

It is appreciated that having regard to the compounds defined above with respect to Formulae I and III, a compound where n is 1 and X is =O is the keto tautomeric form of an otherwise equivalent enol compound where n is 0 and X is OH.

The present invention particularly includes guanine as the base moiety where n is 1, X is =O, Y is $NH_2$ and no double bond exists between position 3 and position 4 i.e. between the carbon ring atom bearing the =O and the adjacent ring nitrogen atom.

Compounds embodying the present invention have surprisingly been found to have enhanced anti-viral activity. In particular, compounds embodying the present invention have been found to have enhanced potency with respect to hepatitis C virus.

The enhanced anti-viral potency of the compounds of the present invention is believed to be due to the presence in the molecule of formula I of the combination of the fused multi-ring entity for Ar in the phosphoramidate moiety and the methylene (—$CH_2$—) group at the β-2' position in the glycoside moiety of the nucleoside, with T, V and T" as set out above.

By $C_{9-30}$aryl is meant an aromatic entity comprising 9 to 30 ring carbon atoms in an aryl format. By $C_{6-30}$heteroaryl is meant an aromatic entity comprising 6 to 30 ring carbon atoms in an aryl format, with at least one aryl ring containing a ring hetero atom.

Suitably, Ar can comprise two, three, four, five or six fused aromatic rings. Preferably, Ar comprises an aryl entity in the form of two or three fused aromatic rings. More preferably, Ar is a two-ring fused aromatic entity selected from $C_9$ to $C_{20}$ aryl and $C_6$ to $C_{20}$ heteroaryl. Where Ar is heteroaryl, suitably 1 to 12 hetero atoms are within the aryl rings and suitably are selected, independently, from 1 to 4 nitrogen atoms, 1 to 4 oxygen atoms and 1 to 4 sulphur atoms. Preferably, the hetero atoms include nitrogen.

Available carbon atoms and/or heteroatoms in the aryl or heteroaryl ring system of Ar may be substituted on the ring with one or more substituents, as set out below with respect to the substituents that may be present on the group Ar. Preferably Ar is unsubstituted.

Suitably, Ar is naphthyl ($C_{10}H_7$) or quinolyl ($C_9H_6N$), each of which may be optionally substituted.

Most suitably, Ar is naphthyl. The naphthyl entity is preferably linked to the O—P entity at the 1 or α position on the naphthyl group, i.e. at a C atom adjacent the fused bond between the two rings in the naphthyl group. Any optional substituent is preferably present at the 4 position. Preferably Ar is unsubstituted 1-naphthyl.

When Ar is quinolyl, it is preferably linked to the O—P entity at the 4 position on the quinolyl group, i.e. on the same ring as that containing the hetero atom N, which N is numbered as position 1. Any substituent present is preferably present at the 6 position, i.e on the ring not containing the hetereo N atom, which N is numbered as position 1.

Preferably T is selected from the group consisting of hydrogen (H—), fluoro (F—), methyl ($CH_3$—) and ethyl ($C_2H_5$—).

Preferably V is selected from the group consisting of hydrogen (H—), fluoro (F—) and OT', where T' is hydrogen (H—) or methyl ($CH_3$—).

Preferably T" is hydrogen (H—).

A preferred combination of T, V and T" is T=H, V=OH and T"=H.

The combination of the above recited preferred entities for Ar with T=H, V=OH and T"=H is especially preferred.

Preferably n is 1 and X is =O. More preferably n is 1, X is =O and Y is $NH_2$ and the nucleoside base moiety corresponds to 9-linked guanine. Where Z is H, the nucleoside base moiety corresponds to unsubstituted 9-linked guanine. Where Z is not H, the nucleoside base moiety corresponds to 8-substituted 9-linked guanine.

Alternatively, preferably n is 0 and X is selected from the group consisting of $NH_2$, F, Cl and $NR_5R_6$ where one of $R_5$ and $R_6$ is H and one of $R_5$ and $R_6$ is $C_{1-6}$alkyl. Where n is 0, X is $NH_2$, Y is H and Z is H, the nucleoside base moiety corresponds to 9-linked adenine.

Preferably, Y is selected from the group consisting of H, F, Cl, $NH_2$ and $NR_5R_6$ where one of $R_5$ and $R_6$ is H and one of $R_5$ and $R_6$ is $C_{1-6}$alkyl.

Preferably, Z is selected from the group consisting of H, F and Cl.

Preferably, Q is O.

Preferably, $R_3$ is alkyl. More preferably, $R_3$ is selected from the group consisting of methyl (—$CH_3$), ethyl ($CH_3CH_2$—), 2-propyl (($CH_3)_2CH$—), n-propyl ($CH_3$—$CH_2$—$CH_2$—), cyclohexyl ($C_6H_{11}$—), 2-butyl (($CH_3)C(H)(CH_2CH_3)$—) and benzyl ($C_6H_5CH_2$—), even more preferably $R_3$ is selected from the group consisting of methyl, ethyl, 2-propyl and benzyl, even more preferably $R_3$ is selected from the group consisting of ethyl and benzyl.

Preferably, $R_4$ is H or, together with $R_1$, comprises (—$(CH_2)_3$—) so as to provide a group corresponding to proline.

Preferably, $R_1$ and $R_2$ are independently selected from the group consisting of H, 2-propyl (($CH_3)_2CH$—), benzyl ($C_6H_5CH_2$—) and —$CH_2$isopropyl (($CH_3)_2C(H)$—$CH_2$—) or are selected such that they correspond to the side chains of a natural amino acid.

Preferably, one of $R_1$ and $R_2$ is methyl (—$CH_3$) and one of $R_1$ and $R_2$ is H, such that the C atom bearing $R_1$ and $R_2$ has chirality L as in natural alanine.

Preferred compounds have in combination the preferred identities for Ar, T, V, T', T'', X, Y, Z, Q, $R_1$, $R_2$, $R_3$ and $R_4$ as set out above.

Particularly preferred compounds have:

n=1, X=O, Y=$NH_2$, Z=H, Q=O, T=H, V=OH and T''=H and are thus derived from guanine; and n=0, X=$NH_2$, Y=Z=H, Q=O, T=H, V=OH and T''=H and are thus derived from adenine.

Each of the particularly preferred compounds set out immediately above and so derived from guanine or adenine is especially preferred when each of Ar, $R_1$, $R_2$, $R_3$ and $R_4$ has the preferred identities set out above, and is especially preferred when Ar is 1-naphthyl and $R_3$ is benzyl or ethyl.

Particularly preferred compounds are described in Examples 2, 3, 4, 6, 7, 8 and 11 and set out in Table II below.

The phosphorus centre in compounds of formula I may be one diastereoisomer $R_P$ or $S_P$ or it may be a mixture of the diastereoisomers $R_P$ or $S_P$. Preferably it is one pure diastereoisomer. Suitably the more active diastereoisomer is selected.

Suitably the pharmaceutical acceptable salts, solvates and prodrugs of compounds of formula I are esters or amides at the 3'-OH of the glycoside moiety of the nucleoside group.

Preferably the process for preparing the compound of formula I includes the step of protecting free OH groups, other than 5' on the glycoside moiety of the nucleoside group. The phosphorochloridate may be prepared from an aryloxy phosphorodichloridate and a suitably protected amino acid derivative. Alternatively, phosphate chemistry may be used with suitable condensing agents.

Each of Ar, $R_1$, $R_2$, $R_3$ and $R_4$ can be substituted with one, two, three, four, five or more substituents independently selected from the group comprising electron donating and electron withdrawing moieties.

Substituents on Ar are suitably independently selected from the group consisting of hydroxy (OH—), acyl (R'C(=O)—), acyloxy (R'C(=O)O—), nitro (—$NO_2$), amino (—$NH_2$), —$SO_3$H, —SH, R'S—, wherein R' is independently selected from the same group set out above as $R_1$; carboxyl (—COOH), $C_{1-6}$esters, $C_{1-6}$aldehyde, cyano (—CN), $C_{1-6}$alkylamino, $C_{1-6}$dialkylamino, thiol, chloro, bromo, fluoro, iodo, $C_{1-6}$alkyl, $C_{2-6}$alkenyl, $C_{1-6}$alkoxy-$C_{1-6}$alkyl, $C_{1-6}$alkoxy-$C_{5-10}$aryl, $C_{5-7}$cycloalkyl, $C_{5-11}$cycloalkyl-$C_{1-6}$alkyl, $C_{5-7}$cycloalkenyl, $C_{5-7}$cycloalkynyl, $C_{5-11}$arylC$_{1-6}$alkyl, $C_{1-6}$alkylC$_{5-11}$aryl, $C_{5-11}$aryl, $C_{1-6}$fluoroalkyl and $C_{2-6}$fluoroalkenyl. Each substituent can be substituted by any other substituent.

Substituents on $R_1$, $R_2$, $R_3$ and $R_4$ are independently selected from the group consisting of hydroxy (—OH), acyl (R'C(C=O)—), acyloxy (R'C(O=)O—), nitro (—$NO_2$), amino (—$NH_2$), amido (—$CONH_2$), —$SO_3$—H, —SH, —SR', wherein R' is independently selected from the same group set out above as $R_1$, carboxyl (—COOH), $C_{1-6}$esters, $C_{1-6}$aldehyde, cyano (CN—), $C_{1-6}$alkylamino, $C_{1-6}$dialkylamino, thiol, chloro, bromo, fluoro, iodo, $C_{5-7}$cycloalkyl, $C_{5-7}$ cycloalkenyl, $C_{5-7}$cycloalkynyl, $C_{5-11}$aryl, $C_{5-11}$aryl $C_{1-6}$alkyl and $C_{5-20}$heterocyclyl. Each substituent can be substituted by any other substituent.

$R_1$ and $R_2$ are suitably independently selected from the group consisting of H, $C_{1-10}$alkyl, $C_{2-10}$alkenyl, $C_{2-10}$alkoxyC$_{1-10}$alkyl, $C_{1-10}$alkoxyC$_{6-10}$aryl, $C_{2-10}$alkynyl, $C_{3-20}$cycloalkyl, $C_{3-20}$cycloalkenyl, $C_{4-20}$cycloalkynyl, and $C_{5-10}$heterocyclyl.

$R_1$ and $R_2$ are suitably selected from the side chains of natural or synthetic amino acids.

$R_1$ and/or $R_2$ are preferably a side chain of a natural amino acid selected from the group consisting of glycine, alanine, valine, leucine, isoleucine, phenylalanine, tyrosine, tryptophan, serine, threonine, lysine, arginine, histidine, aspartic acid, glutamic acid, asparagines, glutamine, cysteine and methionine. Specifically, $R_1$ and/or $R_2$ are preferably selected from the group consisting of H, $CH_3$, —$CH(CH_3)_2$, —$CH_2CH(CH_3)_2$, —$CH(CH_3)(CH_2CH_3)$, —$CH_2Ph$, —$CH_2Ph$-OH, —$CH_2SH$, —$CH_2CH_2SCH_3$, —$CH_2OH$, —$CH(CH_3)(OH)$, —$CH_2CH_2CH_2CH_2NH_3^+$, —$CH_2CH_2CH_2NHC(=NH_2^+)NH_2$, —$CH_2C(O)O$—, —$CH_2CH_2C(O)O$—, —$CH_2C(O)NH_2$, —$CH_2CH_2C(O)NH_2$,

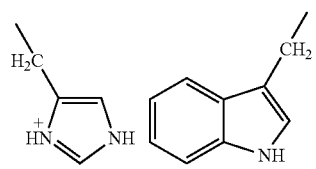

and wherein $R_1$ and $R_4$ together can form a 5-membered heterocyclic ring having the structure

$R_3$ and $R_4$ are suitably independently selected from the group consisting of H, $C_{1-10}$alkyl, $C_{2-10}$alkenyl, $C_{1-10}$alkoxy, $C_{1-10}$alkoxyC$_{1-10}$alkyl, $C_{1-10}$alkoxyC$_{6-10}$aryl, $C_{2-10}$alkynyl, $C_{3-20}$cycloalkyl, $C_{3-20}$cycloalkenyl, $C_{4-20}$cycloalkynyl, and $C_{5-20}$heterocyclyl.

$R_3$ is suitably selected from the group consisting of H, $C_{1-18}$alkyl, $C_{3-20}$cycloalkyl and benzyl.

$R_4$ is suitably selected from the group consisting of H, $C_{1-18}$alkyl, $C_{3-20}$cycloalkyl and $C_{5-20}$heterocyclyl. $R_4$ is particularly suitably selected from the group consisting of H, methyl, ethyl, propyl, butyl, pentyl, hexyl and cyclohexyl.

In a preferred embodiment, $R_1$ and $R_2$ are methyl or are linked to form a closed 5-membered heterocyclic or carbocyclic ring, for example, as present in proline.

As used herein, the term "alkyl" refers to a straight or branched saturated monovalent cyclic or acyclic hydrocarbon radical, having the number of carbon atoms as indicated (or where not indicated, an acyclic alkyl group preferably has 1-20, more preferably 1-6, more preferably 1-4 carbon atoms and a cyclic alkyl group preferably has 3-20, preferably 3-10, more preferably 3-7 carbon atoms), optionally substituted with one, two, three or more substituents independently selected from the group set out above with respect to substituents that may be present on $R_1$, $R_2$, $R_3$ and $R_4$. By way of non-limiting examples, suitable alkyl groups include methyl, ethyl, propyl, butyl, pentyl, hexyl, octyl, nonyl and dodecyl.

As used herein, the term "alkenyl" refers to a straight or branched unsaturated monovalent acyclic or cyclic hydrocarbon radical having one or more C=C double bonds and having the number of carbon atoms as indicated (or where not indicated, an acyclic alkenyl group preferably has 2-20, more preferably 2-6, more preferably 2-4 carbon atoms and a cyclic alkenyl group preferably has 4-20, more preferably 4-6 carbon atoms), optionally substituted with one, two, three or more substituents independently selected from the group set out above with respect to substituents that may be present on $R_1$, $R_2$, $R_3$ and $R_4$. By way of non-limiting examples, suitable alkenyl groups include vinyl, propenyl, butenyl, pentenyl and hexenyl.

As used herein, the term "alkynyl" refers to a straight or branched unsaturated monovalent acyclic or cyclic hydrocarbon radical having one or more triple C≡C bonds and having the number of carbon atoms as indicated (or where not indicated, an acyclic alkynyl group preferably has 2-20, more preferably 2-6, more preferably 2-4 carbon atoms and a cyclic alkynyl group preferably has 7-20, more preferably 8-20 carbon atoms), optionally substituted with one, two, three or more substituents independently selected from the group set out above with respect to substituents that may be present on $R_1$, $R_2$, $R_3$ and $R_4$.

As use herein, the term "alkoxy" or the term "alkyloxy" refers to the group alkyl-O—, where alkyl is as defined above and where the alkyl moiety may optionally be substituted by one, two, three or more substituents as set out above for alkyl. By way of non-limiting examples, suitable alkoxy groups include methoxy, ethoxy, n-propoxy, iso-propoxy, n-butoxy, tert-butoxy, sec-butoxy, n-pentoxy, n-hexoxy and 1,2-dimethylbutoxy. The term "cycloalkyloxy" refers to the group cyclicalkyl-O—, where cyclicalkyl is as defined above and where the cyclicalkyl moiety may be optionally substituted by one, two, three or more substituents as set out above for alkyl.

As used herein, the term "aryloxy" refers to the group aryl-O—, where aryl is as defined below and where the aryl moiety may optionally be substituted by one, two, three or more substituents as set out above with respect to the group Ar.

As used herein, the term "alkoxyalkyl" refers to an alkyl group having an alkoxy substituent. Binding is through the alkyl group. The alkyl moiety and the alkoxy moiety are as defined herein with respect to the definitions of alkyl and alkoxy, respectively. The alkoxy and alkyl moieties may each be substituted by one, two, three or more substituents as set out above with regard to the definition of alkyl.

As used herein, the term "alkoxyaryl" refers to an aryl group having an alkoxy substituent. Binding is through the aryl group. The alkoxy moiety and the aryl moiety are as defined herein with respect to the definitions of alkoxy and aryl, respectively. The alkoxy and aryl moieties may each be substituted by one, two, three or more substituents, as defined herein with regard to the definitions of alkoxy and aryl, respectively.

As used herein, the term "cycloalkylaryl" refers to an aryl group having a cyclic alkyl substitutent. Binding is through the aryl group. The cycloalkyl moiety and the aryl moiety are as defined herein with respect to the definitions of cycloalkyl and aryl, respectively. The cycloalkyl moiety and the aryl moiety may each be optionally substituted by one, two, three or more substituents as set out herein with regard to the definitions of alkyl and aryl, respectively.

Except where otherwise stated with respect to the definition of "Ar", as used herein the term "aryl" refers to a monovalent unsaturated aromatic carbocyclic radical having one, two, three, four, five or six rings, preferably one, two or three rings, which may be fused or bicyclic. An aryl group may optionally be substituted by one, two, three or more substituents as set out above with respect to optional substituents that may be present on the group Ar. Preferred aryl groups are: an aromatic monocyclic ring containing 6 carbon atoms; an aromatic bicyclic or fused ring system containing 7, 8, 9 or 10 carbon atoms; or an aromatic tricyclic ring system containing 10, 11, 12, 13 or 14 carbon atoms. Non-limiting examples of aryl include phenyl and naphthyl. Preferred substituent groups are independently selected from hydroxy (—OH), acyl acyloxy (R'—C(=O)—), acyloxy (R'—C(=O)—O—), nitro (—NO$_2$), amino (—NH$_2$), —SO$_3$H, —SH, —SR', wherein R' is independently selected from the same groups as $R_1$; carboxyl (—COOH), cyano (—CN), $C_{1-6}$alkylamino, $C_{1-6}$dialkylamino, thiol, chloro, bromo, fluoro and iodo.

As used herein, the term "heterocyclyl" refers to a saturated or partially unsaturated heterocyclic ring system having one, two, three, four, five or six rings, preferably one, two or three rings, which may be fused or bicyclic, and having contained within the ring or rings at least one member selected from the group consisting of N, O and S. The prefix "$C_{5-20}$" or "$C_{5-10}$" used before heterocyclyl means, respectively, a five to twenty or a five to ten membered ring system at least one of which members is selected from the group consisting of N, O and S. Preferred heterocyclyl systems are: a monocyclic ring system having five members of which at least one member is a N, O or S atom and which optionally contains one additional O atom or one, two or three additional N atoms; a monocyclic ring having six members of which one, two or three members are a N atom; a bicyclic ring system having nine members of which at least one member is a N, O or S atom and which optionally contains one, two or three additional N atoms; or a bicyclic ring system having ten members of which one, two or three members are a N atom. Examples include, and are not limited to, pyrrolinyl, pyrrolidinyl, 1,3-dioxolanyl, imidazolinyl, imidazolidinyl, pyrazolinyl, pyrazolidinyl, piperidinyl, morpholinyl or piperazinyl.

Available carbon atoms and/or heteroatoms of the "heterocyclyl" ring systems described above may be substituted on the ring with one or more heteroatoms. Where the ring(s) is substituted with one or more heteroatoms selected from oxygen, nitrogen and sulphur, and the ring(s) may include other substituents such as halogen (F, Cl, Br and I). Where the ring(s) is substituted with one or more heteroatoms, preferably there are one or more heteroatom substituents selected from the group consisting of oxygen, nitrogen and/or sulphur. Preferred substituent groups are independently selected from hydroxy, acyl, acyloxy, nitro, amino, SO.sub.3H, SH, SR', wherein R' is independently selected from the same groups as R; carboxyl, cyano, C.sub.1-6alkylamino, C.sub.1-6dialkylamino, thiol, chloro, bromo, fluoro and iodo.

The process is preferably carried out in the presence of a suitable solvent.

Suitable solvents include hydrocarbon solvents such as benzene and toluene; ether type solvents such as diethyl ether, tetrahydrofuran, diphenyl ether, anisole and dimethoxybenzene; halogenated hydrocarbon solvents such as methylene chloride, chloroform and chlorobenzene; ketone type solvents such as acetone, methyl ethyl ketone and methyl isobutyl ketone; alcohol type solvents such as methanol, ethanol, propanol, isopropanol, n-butyl alcohol and tert-butyl alcohol; nitrile type solvents such as acetonitrile, propionitrile and benzonitrile; ester type solvents such as ethyl acetate and butyl acetate; carbonate type solvents such as ethylene carbonate and propylene carbonate; and the like. These may be used singly or two or more of them may be used in admixture.

Preferably an inert solvent is used in the process of the present invention. The term "inert solvent" means a solvent inert under the conditions of the reaction being described in conjunction therewith including, for example, benzene, toluene, acetonitrile, tetrahydrofuran, dimethylformamide, chloroform, methylene chloride (or dichloromethane), diethyl ether, ethyl acetate, acetone, methylethyl ketone, methanol, ethanol, propanol, isopropanol, tert-butanol, dioxane, pyridine, and the like. Tetrahydrofuran is particularly preferred.

Preferably the process of the present invention is carried out under substantially dry conditions.

As used herein, the term "stereoisomer" defines all possible compounds made up of the same atoms bonded by the same sequence of bonds but having different three-dimensional structures which are not interchangeable, which the compounds of the present invention may possess.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixture of stereoisomers, these isomers may be separated by conventional techniques such as preparative chromatography. The compounds may be prepared in stereochemically mixed form or individual enantiomers may be prepared by standard techniques known to those skilled in the art, for example, by enantiospecific synthesis or resolution, formation of diastereomeric pairs by salt formation with an optically active acid, followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

Furthermore, it should be appreciated that the phosphate centre is chiral in the compounds of the present invention and the compounds may exist as Rp and Sp diastereoisomers. The composition of the compound may be mixed Rp and Sp or one pure diastereomer. Preferably the compound is a substantially pure single isomer.

There may be a mixture of 1:1 Rp to Sp diastereomers. Alternatively, there may be a ratios of 1:2, 1:3, 1:4, 1:5, 1:6, 1:7, 1:8, 1:9, 1:10, 1:15, 1:20, 1:50 or 1:100 of Rp to Sp diastereomers or vice versa.

The term "solvate" means a compound of as defined herein, or a pharmaceutically acceptable salt of a compound of structure (I) or (II), wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a hydrate.

The compounds of the present invention may also be present in the form of pharmaceutical acceptable salts. For use in medicine, the salts of the compounds of this invention refer to non-toxic "pharmaceutically acceptable salts." FDA approved pharmaceutical acceptable salt forms (Ref. International J. Pharm. 1986, 33, 201-217; J. Pharm. Sci., 1977, January, 66 (1)) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, maleate, mandelate, mesylate, methylbromide, methylnitrate, methylsulfate, mucate, napsylate, nitrate, pamoate, pantothenate, phosphate, diphospate, polygalacturonate, salicylate, stearate, subacetate, succinate, sulfate, tannate, tartrate, teoclate, tosylate and triethiodide.

Pharmaceutically acceptable basic/cationic salts include, and are not limited to aluminum, benzathine, calcium, chloroprocaine, choline, diethanolamine, ethylenediamine, lithium, magnesium, potassium, procaine, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Pharmaceutically acceptable ester derivatives in which one or more free hydroxy groups are esterified in the form of a pharmaceutically acceptable ester are particularly prodrug esters that may be convertible by solvolysis under physiological conditions to the compounds of the present invention having free hydroxy groups.

Pharmaceutical compositions for use in accordance with the present invention may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen.

The compound having formula I or pharmaceutical composition according to the present invention can be administered to a patient, which may be homo sapiens or animal, by any suitable means.

The medicaments employed in the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.1 to 300 mg per kilogram body weight of the recipient per day. A preferred lower dose is 0.5 mg per kilogrm body weight of recipient per day, a more preferred lower dose is 1 mg per kilogram body weight of recipient per day. A suitable dose is preferably in the range of 1 to 50 mg per kilogram body weight per day, and more preferably in the range of 1 to 10 mg per kilogram body weight per day. The desired dose is preferably presented as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

EXAMPLES

Embodiments of the present invention will now be described by way of example only with respect to the following examples.

Target compounds were prepared by reacting the appropriate nucleoside, or its modified precursor, with the required phosphorochloridate. The latter reagents were prepared by published methods from aryl phosporodichloridates with amino acid ester hydrochlorides. Several examples are given.

Standard Procedure C2

Preparation of 2',3'-cyclopentylidyn-modified-nucleoside phosphoramidates

ᵗBuMgCl (2.0 mol. equivalent) and 2',3'-cyclopentylidene, 4'-azido-cytidine (1.0 mol. equivalent) were dissolved in dry tetrahydrofuran (THF) (31 mol. equivalent) and stirred for 15 minutes. Then a 1M solution of the appropriate phosphorochloridate (2.0 mol. equivalent) in dry THF was added dropwise, then stirred overnight. A saturated solution of $NH_4Cl$ was added and the solvent was removed under reduced pressure to give a yellow solid, which was consequently purified.

Standard Procedure C3

Preparation of phosphoramidates of Modified Nucleoside

2',3'-cyclopentylidene, modified nucleoside phosphoramidates were dissolved in a solution 80% of formic acid in water for 4 hours. The solvent was removed under reduced pressure to give a white solid which was consequently purified.

Standard Procedure C4

Preparation of phosphoramidates of Modified Nucleoside

2',3'-isopropilidene, modified nucleoside phosphoramidates were dissolved in a solution 60% of acetic acid in water at 90° C. overnight. The solvent was removed under reduced pressure to give a white solid which was consequently purified.

Example 1

Synthesis of β-2'-methyl-adenosine (CHC1)

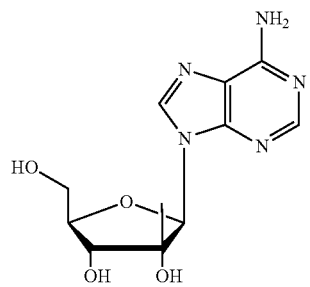

N6-tert-butanoyl-β-2'-methyl-2',3',5'-tribenzoyl-adenosine (400 mg, 0.590 mmol) was added to a solution of MeOH saturated with ammonia, and stirred at room temperature. After 12 hours the solvent was removed and the obtained solid was purified by column chromatography in gradient starting with a mixture of $CHCl_3$/MeOH 9:1 then 8:2. The pure product was obtained as a white solid (120 mg, 0.427 mmol, 72%).

$\delta_H$ ($d_6$-DMSO): 8.47 (1H, s, H8-adenosine), 8.15 (1H, s, H2-adenosine), 7.30 (1H, s, $NH_2$6-adenosine), 5.95 (1H, s, H1'-adenosine), 5.25-5.21 (3H, m, OH5'-adenosine, OH3'-adenosine, OH2'-adenosine), 4.12-4.05 (1H, d, H3'-adenosine, J=8.6 Hz), 3.91 (1H, m, H4'-adenosine), 3.84 (1H, m, H5'-adenosine), 3.70 (1H, m, H5'-adenosine), 0.77 (3H, s, $CH_3$2'-adenosine); $\delta_C$ ($d_6$-DMSO): 156.02 (1C, C6-adenosine), 152.53 (1C, C2-adenosine), 149.01 (1C, C4-adenosine), 138.68 (1C, C8-adenosine), 118.67 (1C, C5-adenosine), 90.78 (1C, C1'-adenosine), 82.52 (1C, C4'-adenosine), 78.46 (1C, C2'-adenosine), 71.63 (1C, C3'-adenosine), 59.47 (1C, C5'-adenosine), 19.83 (1C, CH$_3$-2'-adenosine). Anal. Calc. for C$_{11}$H$_{15}$N$_5$O$_4$: C 46.97%, H 5.38%, N 24.90%. Found: C 46.67%, H 5.22%, N 24.20%.

Example 2

Synthesis of 2',3'-O,O-cyclopentylidyn-β-2'-methyl-adenosine 5'-O-[phenyl(ethoxy-L-alaninyl]phosphate

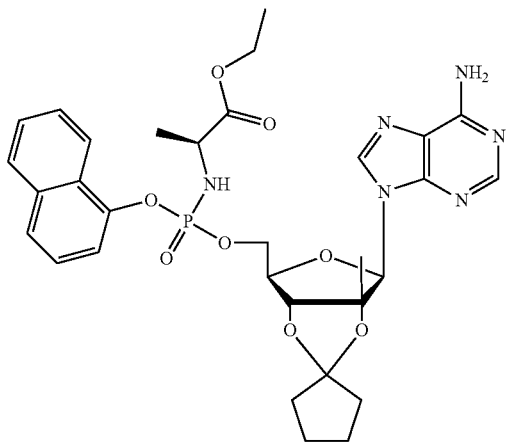

Prepared according to Standard Procedure C2, from 2',3'-O,O-cyclopentylidyn-β-2'-methyl-adenosine (60 mg, 0.172 mmol), $^t$BuMgCl (0.5 ml, 1M solution in THF, 0.519 mmol) and α-naphthyl(ethoxy-L-alaninyl)phosphorochloridate (0.5 ml of solution 1M in THF, 0.519 mmol). The crude was purified by column chromatography, using as eluent CHCl$_3$/MeOH (95:5). The obtained pure product was a white solid (30 mg, 0.046 mmol, 26%).

δ$_P$) (d$_4$-CH$_3$OH): 4.31, 4.26; δ$_H$ (d$_4$-CH$_3$OH): 8.19 (1H, s, H2-adenosine), 8.10 (1H, s, H8-adenosine), 7.88 (1H, m, CH-naphthyl), 7.73 (1H, m, CH-naphthyl), 7.57-7.52 (4H, m, CH-naphthyl), 7.45-7.43 (1H, m, CH-naphthyl), 6.26 (1H, m, H1'-adenosine), 4.56-4.42 (4H, m, H4'-adenosine, H3'-adenosine, 2H5'-adenosine), 4.08 (3H, m, CHα, CH$_2$-ethyl), 2.21-2.09 (2H, m, CH$_2$-cyclopentyl), 1.76-1.71 (6H, m, 3 CH$_2$-cyclopentyl), 1.35 (3H, d, CH$_3$-alanine, J=6.9 Hz), 1.25 (3H, m, CH$_3$-ethyl), 0.95 (3H, s, CH$_3$2'-adenosine).

Synthesis of β-2'-methyl-adenosine 5'-O-[α-naphthyl (ethoxy-L-alaninyl)]phosphate (CHC2)

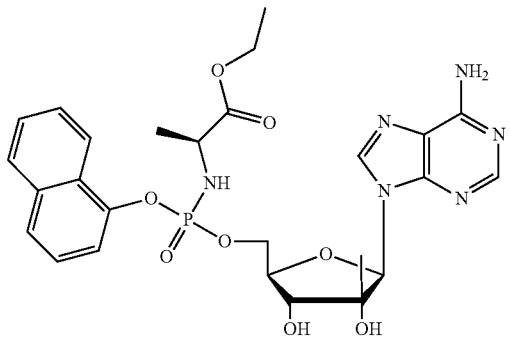

Prepared according to Standard Procedure C3, from 2',3'-O,O-cyclopentylidyn-β-2'-methyl-adenosine 5'-O-[α-naphthyl(ethoxy-L-alaninyl)]phosphate (30 mg, 0.036 mmol), and 10 ml of a solution 80% of HCOOH in water. The crude was purified by column chromatography, using as eluent for the first CHCl$_3$/MeOH (95:5) followed by a semi-preparative HPLC. The obtained pure product was a white solid (4 mg, 0.007 mmol, 19%).

δ$_P$ (d$_4$-CH$_3$OH): 4.23, 4.20; δ$_H$ (d$_4$-CH$_3$OH): 8.24-8.19 (3H, m, H2-adenosine, H8-adenosine, CH-naphthyl), 7.90 (1H, m, CH-naphthyl), 7.63 (1H, CH-naphthyl), 7.53 (4H, m, CH-naphthyl), 7.41 (1H, m, CH-naphthyl), 6.12 (1H, d, H1'-adenosine, J=2.1 Hz), 4.61-4.59 (2H, d, H3'-adenosine, H4'-adenosine), 4.30 (1H, m, H5'-adenosine), 4.02-3.99 (3H, m, CHα, CH$_2$-ethyl), 1.37 (3H, m, CH$_3$-alanine), 1.27 (3H, m, CH$_3$-ethyl), 0.95 (3H, s, CH$_3$-2'-adenosine).

MS (ES) m/e: 609.2 (MNa$^+$, 100%); Accurate mass: C$_{26}$H$_{31}$N$_6$O$_8$NaP required 609.1846, found 609.1839.

Example 3

Synthesis of 2',3'-O,O-cyclopentylidyn-β-2'-methyl-adenosine 5'-O-[phenyl(benzoxy-L-alaninyl)]phosphate

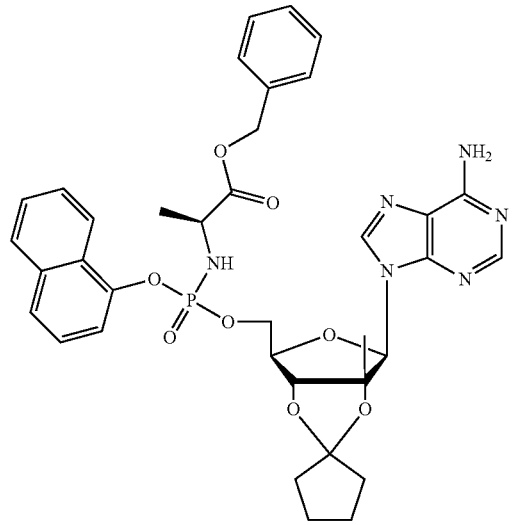

Prepared according to Standard Procedure C2, from 2',3'-O,O-cyclopentylidyn-β-2'-methyl-adenosine (40 mg, 0.115 mmol), $^t$BuMgCl (0.35 ml, 1M solution in THF, 0.345 mmol) and α-naphthyl(benzoxy-L-alaninyl)phosphorochloridate (0.35 ml of solution 1M in THF, 0.345 mmol). The crude was purified by column chromatography, using as eluent CHCl$_3$/MeOH (95:5). The obtained pure product was a white solid (20 mg, 0.028 mmol, 24%).

δ$_P$ (d$_4$-CH$_3$OH): 4.34, 4.18; δ$_H$ (d$_4$-CH$_3$OH): 8.50 (1H, s, H2-adenosine), 8.17 (1H, s, H8-adenosine), 7.90 (1H, m, CH-naphthyl), 7.71 (1H, m, CH-naphthyl), 7.69 (1H, CH-benzyl), 7.55-7.50 (3H, m, CH-naphthyl, 2 CH-benzyl), 7.42-7.27 (6H, m, 4 CH-naphthyl, 2 CH-benzyl), 6.25 (1H, d, H1'-adenosine), 5.10 (2H, s, CH$_2$-benzyl), 4.61 (1H, m, H3'-adenosine), 4.41 (1H, m, H4'-adenosine), 4.15 (1H, m, CHα), 3.95 (1H, m, H5'-adenosine, J=12.2 Hz), 3.85 (1H, m, H5'-adenosine, J=12.2 Hz), 2.12-2.03 (2H, m, CH$_2$-cyclopentyl), 1.79-1.72 (6H, m, 3 CH$_2$-cyclopentyl), 1.37 (3H, d, CH$_3$-alanine, J=7.2 Hz), 0.89 (3H, s, CH$_3$-2'-adenosine).

Synthesis of β-2'-methyl-adenosine 5'-O-[α-naphthyl (benzoxy-L-alaninyl)]phosphate (CHC3)

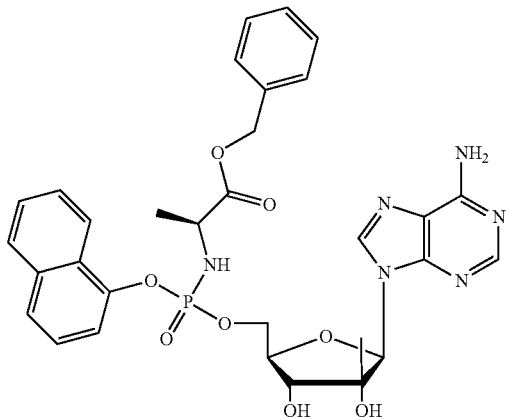

Prepared according to Standard Procedure C3, from 2',3'-O,O-cyclopentylidyn-β-2'-methyl-adenosine 5'-O-[α-naphthyl(benzoxy-L-alaninyl)]phosphate (30 mg, 0.036 mmol), and 10 ml of a solution 80% of HCOOH in water. The crude was purified by column chromatography, using as eluent for the first CHCl$_3$/MeOH (95:5) followed by a semi-preparative HPLC. The obtained pure product was a white solid (5 mg, 0.008 mmol, 21%).

δ$_P$ (d$_4$-CH$_3$OH): 4.25, 4.14; δ$_H$ (d$_4$-CH$_3$OH): 8.04-7.95 (3H, m, H2-adenosine, H8-adenosine, CH-naphthyl), 7.68 (1H, m, CH-naphthyl), 7.48 (1H, m, CH-naphthyl), 7.32-7.23 (3H, m, CH-naphthyl, 2 CH-benzyl), 7.16 (1H, m, CH-naphthyl), 7.05 (6H, m, 3 CH-naphthyl, 3 CH-benzyl), 5.88 (1H, d, H1'-adenosine, J=2.9 Hz), 4.85-4.65 (2H, m, CH$_2$-benzyl), 4.37-4.35 (2H, d, H3'-adenosine, H4'-adenosine), 4.06 (2H, m, H5'-adenosine), 3.88-3.83 (1H, m, CHα), 1.35 (3H, m, CH$_3$-alanine), 0.88 (3H, s, CH$_3$-2'-adenosine).

MS (ES) m/e: 671.2 (MNa$^+$, 100%); Accurate mass: C$_{31}$H$_{33}$N$_6$O$_8$NaP required 671.1990, found 671.1995.

Example 4

Synthesis of 2',3'-O,O-cyclopentylidyn-β-2'-methyl-adenosine 5'-O-[phenyl(tert-butoxy-L-alaninyl)]phosphate

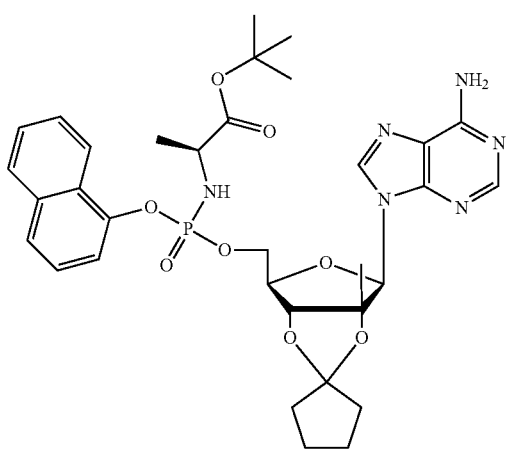

Prepared according to Standard Procedure C2, from 2',3'-O,O-cyclopentylidyn-β-2'-methyl-adenosine (60 mg, 0.172 mmol), $^t$BuMgCl (0.51 ml, 1M solution in THF, 0.51 mmol) and α-naphthyl(tert-butoxy-L-alaninyl)phosphorochloridate (0.5 ml of solution 1M in THF, 0.519 mmol). The crude was purified by column chromatography, using as eluent CHCl$_3$/MeOH (95:5). The obtained pure product was a white solid (27 mg, 0.039 mmol, 22%).

δ$_P$ (d$_4$-CH$_3$OH): 4.37, 4.28; δ$_H$ (d$_4$-CH$_3$OH): 8.21 (1H, s, H2-adenosine), 8.13 (1H, s, H8-adenosine), 7.85 (1H, m, CH-naphthyl), 7.73 (1H, m, CH-naphthyl), 7.57-7.52 (4H, m, CH-naphthyl), 7.43-7.41 (1H, m, CH-naphthyl), 6.25 (1H, m, H1'-adenosine), 4.55-4.40 (4H, m, H4'-adenosine, H3'-adenosine, 2H5'-adenosine), 4.05 (1H, m, CHα), 2.20-2.12 (2H, m, CH$_2$-cyclopentyl), 1.79-1.69 (6H, m, 3 CH$_2$-cyclopentyl), 1.36 (9H, 3 CH$_3$-tert-butyl), 1.25 (3H, d, CH$_3$-alanine, J=6.9 Hz), 0.96 (3H, s, CH$_3$-2'-adenosine).

Synthesis of β-2'-methyl-adenosine 5'-O-[α-naphthyl (tert-butoxy-L-alaninyl)]phosphate (CHC4)

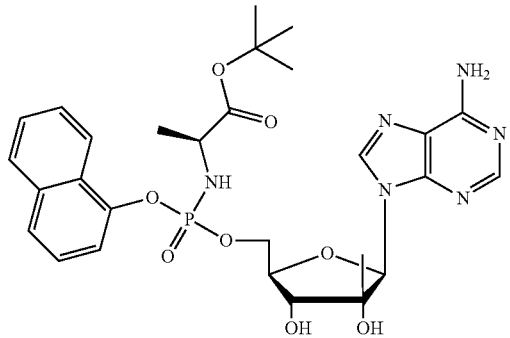

Prepared according to Standard Procedure C3, from 2',3'-O,O-cyclopentylidyn-β-2'-methyl-adenosine 5'-O-[α-naphthyl(tert-butoxy-L-alaninyl)]phosphate (27 mg, 0.039 mmol), and 10 ml of a solution 80% of HCOOH in water. The crude was purified by column chromatography, using as eluent for the first CHCl$_3$/MeOH (95:5) followed by a semi-preparative HPLC. The obtained pure product was a white solid (10 mg, 0.016 mmol, 41%).

δ$_P$ (d$_4$-CH$_3$OH): 4.20, 4.08; δ$_H$ (d$_4$-CH$_3$OH): 8.20-8.15 (3H, m, H2-adenosine, H8-adenosine, CH-naphthyl), 7.81 (1H, m, CH-naphthyl), 7.60 (1H, CH-naphthyl), 7.54 (4H, m, CH-naphthyl), 7.39 (1H, m, CH-naphthyl), 6.15 (1H, d, H1'-adenosine), 4.63-4.57 (2H, d, H3'-adenosine, H4'-adenosine), 4.31 (1H, m, H5'-adenosine), 4.00-3.97 (1H, m, CHα), 1.39 (9H, 3 CH$_3$-tert-butyl), 1.27 (3H, m, CH$_3$-alanine), 0.97 (3H, s, CH$_3$-2'-adenosine).

Example 5

Synthesis of β-2'-methyl-guanosine (CHC5)

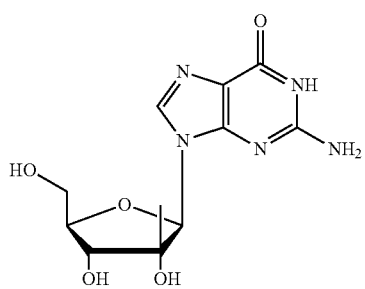

N2-acetyl-β-2'-methyl-2',3',5'-tribenzoyl-guanosine (1.42 g, 2.18 mmol) was added to a solution of MeOH saturated with ammonia, and stirred at room temperature. After 12 hours the solvent was removed and the obtained solid was purified by column chromatography using as eluent a mixture of CHCl$_3$/MeOH 8:2. The pure product was obtained as a white solid (565 mg, 1.90 mmol, 87%).

$\delta_H$ (d$_6$-DMSO): 10.52 (1H, s, NH1-guanosine), 8.48 (1H, s, H8-guanosine), 6.52 (2H, s, NH$_2$2-guanosine), 5.73 (1H, s, H1'-guanosine), 5.24 (1H, d, OH3'-guanosine, J=6.3 Hz), 5.11 (1H, m, OH5'-guanosine), 5.03 (1H, s, OH2'-guanosine), 3.97 (1H, m, H3'-guanosine), 3.85-3.79 (2H, m, H4', H5'-guanosine), 3.66 (1H, d, H5'-guanosine, J=12.2 Hz), 0.81 (3H, s, CH$_3$-2'-guanosine); $\delta_C$ (d$_6$-DMSO): 156.72 (1C, C6-guanosine), 153.68 (1C, C2-guanosine), 150.77 (1C, C4-guanosine), 135.07 (1C, C8-guanosine), 116.38 (1C, C5-guanosine), 90.10 (1C, C1'-guanosine), 82.30 (1C, C3'-guanosine), 78.52 (1C, C2'-guanosine), 71.63 (1C, C4'-guanosine), 59.40 (1C, C5'-guanosine), 19.96 (1C, CH$_3$-2'-guanosine).

MS (ES) m/e: 320.2 (MNa$^+$, 100%); Accurate mass: C$_{11}$H$_{15}$N$_5$O$_5$Na required 320.0968, found 320.0971.

Example 6

Synthesis of 2',3'-O,O-isopropylidyn-β-2'-methyl-guanosine 5'-O-[phenyl(benzoxy-L-alaninyl)]phosphate

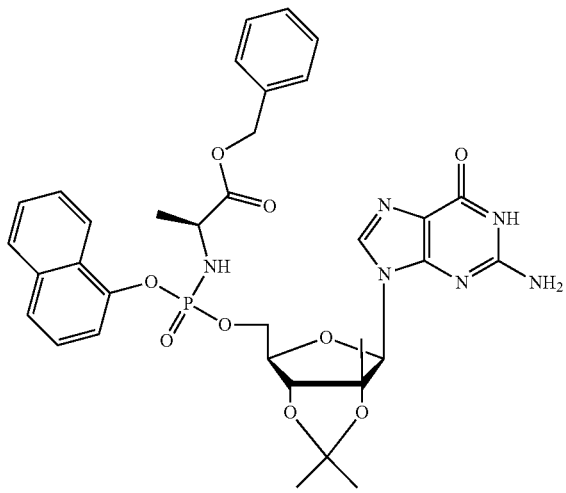

Prepared according to Standard Procedure C2, from 2',3'-O,O-isopropylidyn-β-2'-methyl-guanosine (170 mg, 0.503 mmol), $^t$BuMgCl (1.0 ml, 1M solution in THF, 1.006 mmol) and α-naphthyl(benzoxy-L-alaninyl)phosphorochloridate (1.0 ml of solution 1M in THF, 1.006 mmol). The crude was purified by column chromatography, using as eluent CHCl$_3$/MeOH (95:5). The obtained pure product was a white solid (70 mg, 0.098 mmol, 19%).

$\delta_P$ (d$_4$-CH$_3$OH): 4.53, 4.40; $\delta_H$ (d$_4$-CH$_3$OH): 8.28 (1H, s, H8-guanosine), 7.84 (1H, m, CH-naphthyl), 7.77-7.71 (1H, m, CH-benzyl), 7.55-7.49 (4H, m, 2 CH-naphthyl, 2 CH-benzyl), 7.44-7.29 (6H, m, 4 CH-naphthyl, 2 CH-benzyl), 6.06 (1H, d, H1'-guanosine), 5.10 (2H, s, CH$_2$-benzyl), 4.59 (1H, m, H3'-guanosine), 4.52-4.45 (1H, m, H4'-guanosine), 4.34 (2H, H5' guanosine), 4.14 (1H, m, CHα), 1.59 (3H, d, CH$_3$-isopropylidine, J=10.4 Hz), 1.37 (6H, d, CH$_3$-alanine, CH$_3$-isopropylidine), 0.99 (3H, d, CH$_3$-2'-guanosine, J=20.11 Hz).

Synthesis of β-2'-methyl-guanosine 5'-O-[α-naphthyl(benzoxy-L-alaninyl)]phosphate (CHC6)

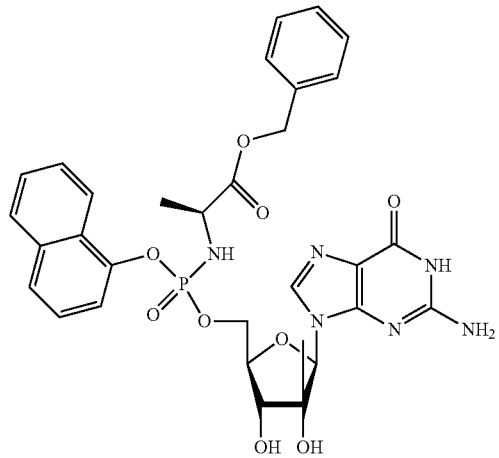

Prepared according to Standard Procedure C4, from 2',3'-O,O-isopropylidyn-β-2'-methyl-guanosine 5'-O[α-naphthyl(benzoxy-L-alaninyl)]phosphate (70 mg, 0.098 mmol), and 10 ml of a solution 60% of CH$_3$COOH in water at 90° C. for 15 hours. The crude was purified by column chromatography, using as eluent for the first CHCl$_3$/MeOH (85:5) followed by a semi-preparative HPLC. The obtained pure product was a white solid (12 mg, 0.018 mmol, 18%).

$\delta_P$ (d$_4$-CH$_3$OH): 4.25, 4.14; $\delta_H$ (d$_4$-CH$_3$OH): 8.17 (1H, m, H8-guanosine), 7.88 (1H, m, CH-naphthyl), 7.79 (1H, m, CH-naphthyl), 7.53 (2H, m, CH-naphthyl, CH-benzyl), 7.42-7.40 (1H, m, CH-naphthyl), 7.36-7.21 (7H, m, 3 CH-naphthyl, 4 CH-benzyl), 6.05 (1H, d, H1'-guanosine, J=8.4 Hz), 5.15-4.90 (2H, m, CH$_2$-benzyl), 4.58-4.49 (2H, d, H3'-guanosine, H4'-guanosine), 4.44-4.34 (2H, m, H5'-guanosine), 4.17-4.11 (1H, m, CHα), 1.37 (3H, m, CH$_3$-alanine), 1.00 (3H, s, CH$_3$-2'-guanosine).

MS (ES) m/e: 687.2 (MNa$^+$, 100%); Accurate mass: C$_{31}$H$_{33}$N$_6$O$_9$NaP required 687.1954, found 687.1944.

Example 7

Synthesis of 2',3'-O,O-isopropylidyn-β-2'-methyl-guanosine 5'-O-[phenyl(ethoxy-L-alaninyl)]phosphate

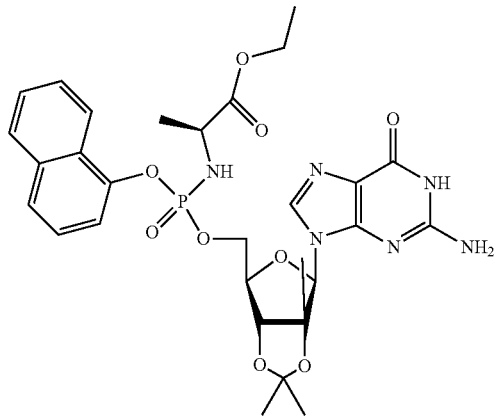

Prepared according to Standard Procedure C2, from 2',3'-O,O-isopropylidyn-β-2'-methyl-guanosine (220 mg, 0.652 mmol), ᵗBuMgCl (1.3 ml, 1M solution in THF, 1.30 mmol) and α-naphthyl(ethoxy-L-alaninyl)phosphorochloridate (1.3 ml of solution 1M in THF, 1.30 mmol). The crude was purified by column chromatography, using as eluent CHCl$_3$/MeOH (95:5). The obtained pure product was a white solid (35 mg, 0.054 mmol, 9%).

$\delta_P$ (d$_4$-CH$_3$OH): 4.41, 4.32; $\delta_H$ (d$_4$-CH$_3$OH): 8.18 (1H, s, H8-guanosine), 7.88 (1H, m, CH-naphthyl), 7.73 (1H, m, CH-naphthyl), 7.59-7.52 (4H, m, 4 CH-naphthyl), 7.46-7.42 (1H, m, CH-naphthyl), 6.08 (1H, d, H1'-guanosine), 4.62-4.40 (4H, m, H3'-guanosine, H4'-guanosine, H5'guanosine), 4.11-4.09 (3H, m, CHα, CH$_2$-ethyl), 1.59 (3H, d, CH$_3$-isopropylidine, J=13.2 Hz), 1.37 (6H, m, CH$_3$-alanine, CH$_3$-isopropylidine), 1.20 (3H, m, CH$_3$-ethyl), 1.00 (3H, m, CH$_3$-2'-guanosine).

Synthesis of β-2'-methyl-guanosine 5'-O-[α-naphthyl(ethoxy-L-alaninyl)]phosphate (CHC7)

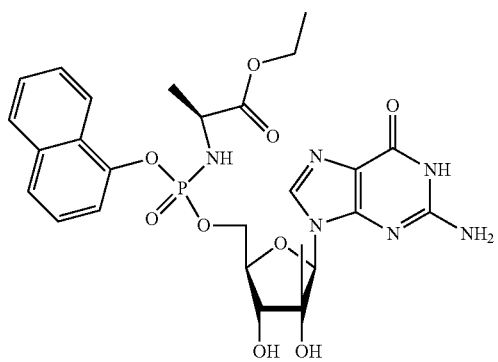

Prepared according to Standard Procedure C4, from 2',3'-O,O-isopropylidyn-β-2'-methyl-guanosine 5'-O-[α-naphthyl(ethoxy-L-alaninyl)]phosphate (35 mg, 0.054 mmol), and 10 ml of a solution 60% of CH$_3$COOH in water at 90° C. for 15 hours. The crude was purified by column chromatography, using as eluent for the first CHCl$_3$/MeOH (85:5) followed by a semi-preparative HPLC. The obtained pure product was a white solid (10 mg, 0.018 mmol, 31%).

$\delta_P$ (d$_4$-CH$_3$OH): 4.25, 4.14; $\delta_H$ (d$_4$-CH$_3$OH): 8.18 (1H, m, H8-guanosine), 7.87 (1H, m, CH-naphthyl), 7.71 (1H, m, CH-naphthyl), 7.53 (4H, m, 4 CH-naphthyl), 7.51-7.40 (1H, m, CH-naphthyl), 5.93 (1H, d, H1'-guanosine), 4.62-4.57 (2H, m, H3'-guanosine, H4'-guanosine), 4.24 (2H, m, H5'guanosine), 4.03-3.98 (3H, m, CHα, CH$_2$-ethyl), 1.31 (3H, d, CH$_3$-alanine, J=7.9 Hz), 1.15 (3H, m, CH$_3$-ethyl), 1.00 (3H, m, CH$_3$-2'-guanosine).

MS (ES) m/e: 625.3 (MNa$^+$, 100%); Accurate mass: C$_{26}$H$_{31}$N$_6$O$_9$NaP required 625.1795, found 6251788.

Anal. Calc. for C$_{26}$H$_{31}$N$_6$O$_9$P: C 51.83%, H 5.19%, N 13.95%. Found: C 51.86%, H 5.10%, N 12.04%.

Example 8

Synthesis of 2',3'-O,O-isopropylidyn-β-2'-methyl-guanosine 5'-O-[phenyl(tert-butoxy-L-alaninyl)]phosphate

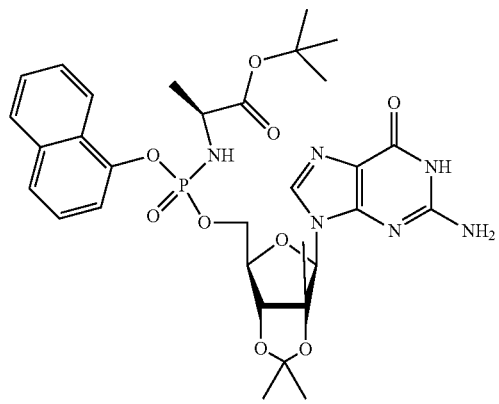

Prepared according to Standard Procedure C2, from 2',3'-O,O-isopropylidyn-β-2'-methyl-guanosine (120 mg, 0.355 mmol), ᵗBuMgCl (0.70 ml, 1M solution in THF, 0.711 mmol) and α-naphthyl(tert-butoxy-L-alaninyl)phosphorochloridate (0.70 ml of solution 1M in THF, 0.711 mmol). The crude was purified by column chromatography, using as eluent CHCl$_3$/MeOH (95:5). The obtained pure product was a white solid (24 mg, 0.036 mmol, 10%).

$\delta_P$ (d$_4$-CH$_3$OH): 4.41, 4.32; $\delta_H$ (d$_4$-CH$_3$OH): 8.20 (1H, s, H8-guanosine), 7.89 (1H, m, CH-naphthyl), 7.73 (1H, m, CH-naphthyl), 7.59-7.54 (4H, m, 4 CH-naphthyl), 7.49-7.42 (1H, m, CH-naphthyl), 6.07 (1H, d, H1'-guanosine), 4.62-4.40 (4H, m, H3'-guanosine, H4'-guanosine, 2H5'guanosine), 3.99-3.86 (1H, m, CHα), 1.58 (3H, d, CH$_3$-isoprpylidine, J=13.7 Hz), 1.44 (9H, s, 3 CH$_3$-tert-butyl), 1.38-1.34 (6H, m, CH$_3$-alanine, CH$_3$-isoprpylidine), 1.01 (3H, m, CH$_3$2'-guanosine).

Synthesis of β-2'-methyl-guanosine 5'-O-[α-naphthyl(tert-butoxy-L-alaninyl)]phosphate (CHC8)

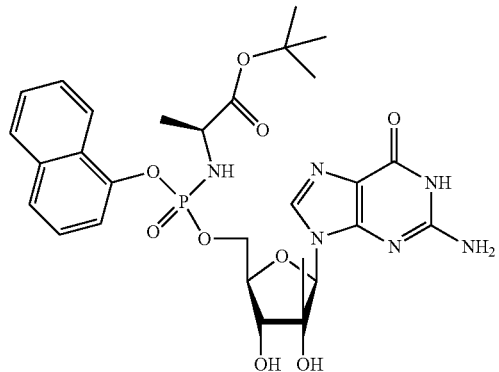

Prepared according to Standard Procedure C4, from 2',3'-O,O-isopropylidyn-β-2'-methyl-guanosine 5'-O-[α-naphthyl(tert-butoxy-L-alaninyl)]phosphate (24 mg, 0.036 mmol), and 10 ml of a solution 60% of $CH_3COOH$ in water. The crude was purified by column chromatography, using as eluent for the first $CHCl_3$/MeOH (85:5) followed by a semi-preparative HPLC. The obtained pure product was a white solid (4 mg, 0.018 mmol, 17%).

$δ_P$ ($d_4$-$CH_3OH$): 4.23, 4.10; $δ_H$ ($d_4$-$CH_3OH$): 8.20 (1H, m, H8-guanosine), 7.85 (1H, m, CH-naphthyl), 7.67 (1H, m, CH-naphthyl), 7.57 (4H, m, 4 CH-naphthyl), 7.53-7.43 (1H, m, CH-naphthyl), 6.00 (1H, d, H1'-guanosine), 4.61-4.55 (2H, m, H3'-guanosine, H4'-guanosine), 4.25 (2H, m, 2H5'guanosine), 4.00-3.97 (1H, m, CHα), 1.47 (9H, s, 3 $CH_3$-tert-butyl), 1.36 (3H, m, $CH_3$-alanine), 1.00 (3H, m, $CH_3$2'-guanosine).

Example 9

Synthesis of 2',3'-O,O-isopropylidene-β-2'-methyl-guanosine 5'-O-[phenyl(benzoxy-L-alaninyl)]phosphate

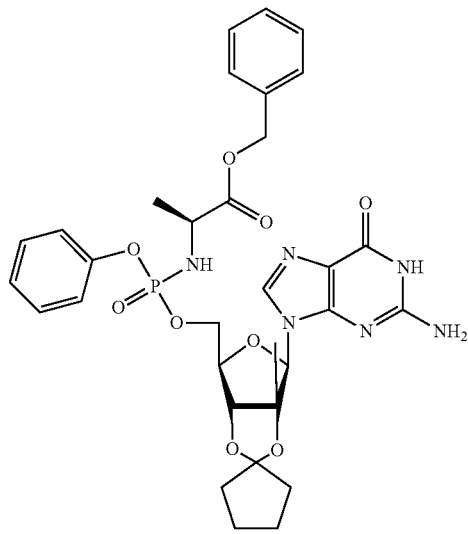

Prepared according to Standard Procedure C2, from 2',3'-O,O-isopropylidene-β-2'-methyl-guanosine (120 mg, 0.355 mmol), $^tBuMgCl$ (1.0 ml, 1M solution in THF, 1.07 mmol) and phenyl(benzoxy-L-alaninyl)phosphorochloridate (1.0 ml of solution 1M in THF, 1.07 mmol). The crude was purified by column chromatography, using as eluent $CHCl_3$/MeOH (9:1) followed by semi-preparative HPLC. The obtained pure product was a white solid (40 mg, 0.061 mmol, 17%).

$δ_P$ ($d_4$-$CH_3OH$): 4.63, 4.37; $δ_H$ ($d_4$-$CH_3OH$): 7.85 (1H, d, H8-guanosine, J=5.7 Hz), 7.36-7.34 (5H, m, 2 CH-phenyl, 3 CH-benzyl), 7.33-7.26 (5H, m, 2 CH-benzyl, 3 CH-phenyl), 6.02 (1H, d, H1'-guanosine, J=11.4 Hz), 5.16 (2H, s, $CH_2$-benzyl), 4.67 (1H, d, H3'-guanosine, J=1.1 Hz), 4.54-4.43 (1H, m, H4'-guanosine), 4.31 (2H, H5'guanosine), 4.10 (1H, m, CHα), 1.61 (3H, s, $CH_3$-isopropylidine), 1.53 (3H, s, $CH_3$-isopropylidine), 1.39 (3H, d, $CH_3$-alanine, J=8.4 Hz), 1.00 (3H, s, $CH_3$-2'-guanosine).

Synthesis of β-2'-methyl-guanosine 5'-O-[phenyl(benzoxy-L-alaninyl)]phosphate (CHC9)

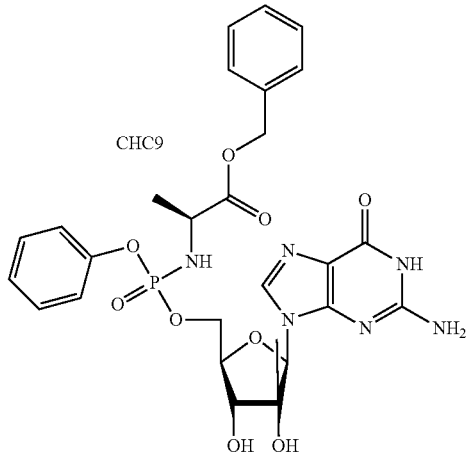

Prepared according to Standard Procedure C4, from 2',3'-O,O-isopropylidene-β-2'-methyl-guanosine 5'-O-[phenyl(benzoxy-L-alaninyl)]phosphate (40 mg, 0.061 mmol), and 10 ml of a solution 60% of $CH_3COOH$ in water at 90° C. for 15 hours. The crude was purified by column chromatography, using as eluent for the first $CHCl_3$/MeOH (85:5) followed by a semi-preparative HPLC. The obtained pure product was a white solid (15 mg, 0.024 mmol, 40%).

$δ_P$ ($d_4$-$CH_3OH$): 4.27, 4.10; $δ_H$ ($d_4$-$CH_3OH$): 7.92 (1H, d, H8-guanosine, J=8.3 Hz), 7.37-7.29 (5H, m, 2 CH-phenyl, 3 CH-benzyl), 7.25-7.18 (5H, m, 2 CH-benzyl, 3 CH-phenyl), 5.96 (1H, d, H1'-guanosine, J=2.3 Hz), 5.15 (2H, s, $CH_2$-benzyl), 4.43-4.35 (2H, m, H3'-guanosine, H4'-guanosine), 4.33-4.28 (1H, m, H5'-guanosine), 4.24-4.19 (1H, m, H5'-guanosine), 4.08-3.93 (1H, m, CHα), 1.35 (3H, m, $CH_3$-alanine), 1.24 (3H, s, $CH_3$-2'-guanosine).

Example 10

Synthesis of 2',3'-O,O-isopropylidene-β-2'-methyl-guanosine 5'-O-[phenyl(methoxy-L-alaninyl)]phosphate

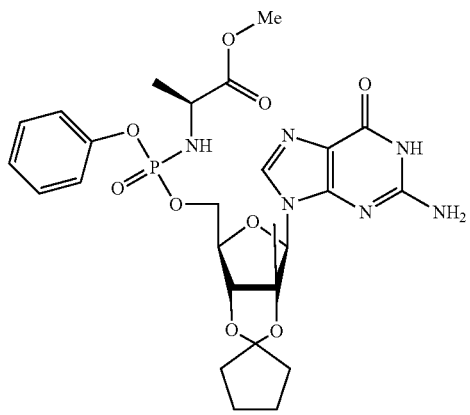

Prepared according to Standard Procedure C2, from 2′,3′-O,O-isopropylidene-β-2′-methyl-guanosine (130 mg, 0.385 mmol), ᵗBuMgCl (0.96 ml, 1M solution in THF, 0.96 mmol) and α-naphthyl(methoxy-L-alaninyl)phosphorochloridate (0.96 ml of solution 1M in THF, 0.96 mmol). The crude was purified by column chromatography, using as eluent CHCl₃/MeOH (97:3). The obtained pure product was a white solid (26 mg, 0.041 mmol, 11%).

δ$_P$ (d₄-CH₃OH): 4.51, 4.45; δ$_H$ (d₄-CH₃OH): 8.21 (1H, d, H8-guanosine, J=7.5 Hz), 7.91-7.89 (1H, m, CH-naphthyl), 7.73 (1H, m, CH-naphthyl), 7.58-7.53 (4H, m, 4 CH-naphthyl), 7.48-7.45 (1H, m, CH-naphthyl), 6.09 (1H, d, H1′-guanosine, J=7.4 Hz), 4.63 (1H, d, H3′-guanosine, J=3.0 Hz), 4.57-4.53 (2H, m, H4′-guanosine), 4.43-4.41 (2H, m, H5′guanosine), 4.12-4.05 (1H, m, CHα), 3.62 (3H, d, CH₃-methyl, J=10.1 Hz), 1.59 (3H, d, CH₃-isopropylidine, J=7.9 Hz), 1.40 (3H, d, CH₃-alanine, J=3.4 Hz), 1.35 (3H, d, CH₃-isopropylidine, J=7.2 Hz), 1.05 (3H, d, CH₃-2′-guanosine, J=7.0 Hz).

Synthesis of β-2′-methyl-guanosine 5′-O-[α-naphthyl (methoxy-L-alaninyl)]phosphate (CHC10)

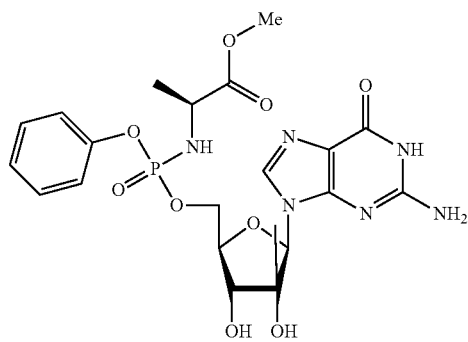

Prepared according to Standard Procedure C4, from 2′,3′-O,O-isopropylidene-β-2′-methyl-guanosine 5′-O-[α-naphthyl(methoxy-L-alaninyl)]phosphate (26 mg, 0.041 mmol), and 10 ml of a solution 60% of CH₃COOH in water at 90° C. for 15 hours. The crude was purified by column chromatography, using as eluent for the first CHCl₃/MeOH (92:8). The obtained pure product was a white solid (4.1 mg, 0.007 mmol, 17%).

δ$_P$ (d₄-CH₃OH): 4.35, 4.26; δ$_H$ (d₄-CH₃OH): 8.20 (1H, d, H8-guanosine, J=5.8 Hz), 7.91-7.87 (2H, m, CH-naphthyl), 7.70 (1H, m, CH-naphthyl), 7.58-7.52 (3H, m, 3 CH-naphthyl), 7.50-7.41 (1H, m, CH-naphthyl), 5.93 (1H, s, H1′-guanosine), 4.58-4.56 (2H, m, H3′-guanosine, H4′-guanosine), 4.29-4.21 (2H, m, H5′guanosine), 4.06-4.03 (1H, m, CHα), 3.56 (3H, d, CH₃-methyl, J=1.7 Hz), 1.31 (3H, d, CH₃-alanine, J=7.4 Hz), 1.00 (3H, d, CH₃-2′-guanosine, J=12.4 Hz).

Example 11

Synthesis of 2′,3′-O,O-isopropylidene-β-2′-methyl-guanosine 5′-O-[phenyl(methoxy-L-alaninyl)]phosphate

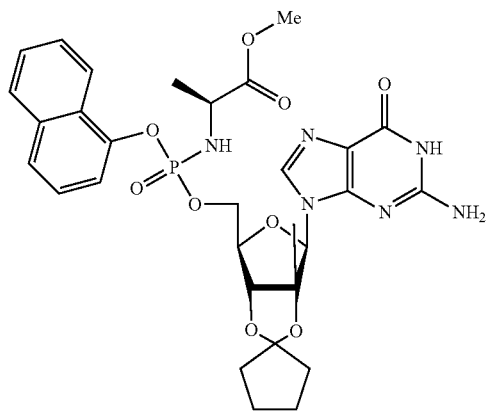

Prepared according to Standard Procedure C2, from 2′,3′-O,O-isopropylidene-β-2′-methyl-guanosine (140 mg, 0.415 mmol), ᵗBuMgCl (1.04 ml, 1M solution in THF, 1.04 mmol) and phenyl(methoxy-L-alaninyl)phosphorochloridate (1.04 ml of solution 1M in THF, 1.04 mmol). The crude was purified by column chromatography, using as eluent CHCl₃/MeOH (97:3). The obtained pure product was a white solid (21 mg, 0.036 mmol, 9%).

δ$_P$ (d₄-CH₃OH): 4.09, 3.91; δ$_H$ (d₄-CH₃OH): 7.88, 7.80 (1H, d, H8-guanosine), 7.41-7.35 (2H, m, CH-phenyl), 7.30-7.20 (3H, m, 3 CH-phenyl), 6.14 (1H, d, H1′-guanosine, J=11.8 Hz), 4.69 (1H, d, H3′-guanosine, J=2.9 Hz), 4.49-4.39 (3H, m, H4′-guanosine, H5′guanosine), 4.04-3.99 (1H, m, CHα), 3.70 (3H, d, CH₃-methyl, J=12.7 Hz), 1.63 (3H, d, CH₃-isopropylidine, J=2.3 Hz), 1.44 (3H, d, CH₃-alanine, J=3.1 Hz), 1.41 (3H, d, CH₃-isopropylidine, J=6.8 Hz), 1.10 (3H, d, CH₃-2′-guanosine, J=6.5 Hz).

Synthesis of β-2′-methyl-guanosine 5′-O-[phenyl (methoxy-L-alaninyl)]phosphate (CHC11)

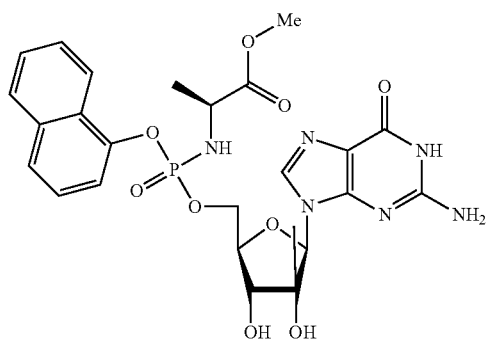

Prepared according to Standard Procedure C4, from 2',3'-O,O-isopropylidene-β-2'-methyl-guanosine 5'-O-[phenyl (methoxy-L-alaninyl)]phosphate (21 mg, 0.036 mmol), and 10 ml of a solution 60% of $CH_3COOH$ in water at 90° C. for 15 hours. The crude was purified by column chromatography, using as eluent for the first $CHCl_3$/MeOH (92:8). The obtained pure product was a white solid (7.0 mg, 0.013 mmol, 36%).

$\delta_P$ ($d_4$-$CH_3OH$): 4.15, 3.90; $\delta_H$ ($d_4$-$CH_3OH$): 8.96 (1H, br, H8-guanosine), 7.40-7.35 (2H, m, CH-phenyl), 7.29-7.20 (3H, m, 3 CH-phenyl), 6.08 (1H, d, H1'-guanosine, J=8.5 Hz), 4.55-4.49 (2H, m, H3'-guanosine, H4'-guanosine), 4.26 (1H, m, H5'guanosine), 4.17-4.11 (1H, m, H5'-guanosine), 4.00-3.97 (1H, m, CHα), 3.73 (3H, d, $CH_3$-methyl, J=11.1 Hz), 1.36 (3H, d, $CH_3$-alanine, J=7.1 Hz), 1.41 (3H, d, $CH_3$-iso-propylidine, J=6.8 Hz), 1.14 (3H, d, $CH_3$-2'-guanosine, J=4.9 Hz).

Each of compounds CHC1 to CHC9, as prepared according to Examples 1 to 11, respectively, was tested for its potency with respect to HCV.

The anti-HCV assays employed were:

Anti-HCV assay in Huh 7 cells. Huh 7 cells containing subgenomic HCV replicons $I_{389}$luc-ubi-neo/NS3-3'/5.1 (Huh 5-2) or $I_{377}$/NS3-3'/wt (Huh 9-13) have been described (Lohmann V, Korner F, Koch J, Herian U, Theilmann L, Bartenschlager R. (1999) Replication of subgenomic hepatitis C virus RNAs in a hepatoma cell line. Science 285:110-113. Lohmann V, Korner F, Dobierzewska A, Bartenschlager R. (2001) Mutations in hepatitis C virus RNAs conferring cell culture adaptation. J Virol. 75:1437-1449.). Cells were grown in Dulbecco's modified Eagle's Medium (DMEM; Gibco, Merelbeke, Belgium) supplemented with 10% heat-inactivated fetal bovine serum (FCS) (Integro, Zaandam, The Netherlands), 1× non-essential amino acids (Gibco), 100 IU/ml penicillin (Gibco), 100 μg/ml streptomycin (Gibco) and 250 μg/ml Geneticin (G418, Gibco) for Huh 5-2 cells, 1000 μg/ml G418 for Huh 9-13 cells Anti-HCV Assay in Huh 5-2 Cells.

Huh 5-2 cells were seeded at a density of 5×10³ per well in a tissue culture treated white 96-well view plate (Packard, Canberra, Canada) in complete DMEM supplemented with 250 μg/ml G418. Following incubation for 24 h at 37° C. (5% $CO_2$) medium was removed and serial dilutions in complete DMEM (without G418) of the test compounds were added in a total volume of 100 μl. After 4 days of incubation at 37° C., cell culture medium was removed and luciferase activity was determined using the Steady-Glo luciferase assay system (Promega, Leiden, The Netherlands); the luciferase signal was measured using a Luminoskan Ascent (Thermo, Vantaa, Finland). The 50% effective concentration ($EC_{50}$) was defined as the concentration of compound that reduced the luciferase signal by 50%.

Anti-HCV Assay in Huh 9-13 Cells.

Huh 9-13 cells were seeded at a density of 5×10³ cells per well in 96-well cell culture plates in complete DMEM supplemented with 1000 μg/ml G418. Following incubation for 24 h at 37° C. cell culture medium was removed and serial dilutions of the test compounds in complete DMEM without G418 were added in a total volume of 100 μl. After 4 days of incubation at 37° C., cell culture fluid was removed and monolayers were washed once with phosphate-buffered saline. Cells were lysed in 350 μl RLT buffer (Qiagen, Venlo, The Netherlands) according to the Manufacturer's instruction. Lysates were stored at −80° C. until further use.

RT-qPCR.

A 25 μL RT-qPCR reaction contained 12.5 μl 2× reaction buffer (Eurogentec, Seraing, Belgium), 6.3 μl $H_2O$, 5 μl total cellular RNA extract and in the case of Huh 9-13 and HuH6 samples 300 nmol/L neo-forward primer [5'-CCG GCT ACC TGC CCA TTC-3'], 300 nmol/L neo-reverse primer [5'-CCA GAT CAT CCT GAT CGA CAA G-3'], 300 nmol/L neo-probe [5'-FAM-ACA TCG CAT CGA GCG AGC ACG TAC-TAMRA-3'] or for Huh-mono samples 300 nmol/L UTR-forward primer [5'-ACG CAG AAA GCG TCT AGC CAT GGC GTT AGT-3'], 300 nmol/L UTR-reverse primer [5'-TCC CGG GGC ACT CGC AAG CAC CCT ATC AGG-3'], 300 nmol/L UTR-probe [5'-FAM-TGG TCT GCG GAA CCG GTG AGT ACA CC-TAMRA-3']. The RT step was performed at 48° C. for 30 minutes, 15 minutes at 95° C. and subsequent PCR amplification of 40 cycles of denaturation at 94° C. for 20 seconds and annealing and extension at 60° C. for 1 minute in an ABI 7000 sequence detector. The 50% effective concentration ($EC_{50}$) was defined as the concentration of compound that reduced replicon RNA content by 50%.

The results in terms of HCV $EC_{50}/\mu M$ and $CC_{50}/\mu M$ are given in Table I below.

In Table I:

A refers to 9-linked adenine, G refers to 9-linked guanine, Nap refers to 1-naphthyl (—$C_{10}H_9$), Ph refers to phenyl (—$C_6H_5$), Et refers to ethyl ($CH_3CH_2$—), Bn refers to benzyl ($C_6H_5CH_2$—), t-Bu refers to tertiary butyl (($CH_3$)$_3C$—) and Me refers to methyl ($CH_3$—).

TABLE I

| Compound | Base | Ar | $R_3$ | HCV Huh 5-2 $EC_{50}/\mu M$ | HCV Huh 9-13 $EC_{50}/\mu M$ | $CC_{50}/\mu M$ |
|---|---|---|---|---|---|---|
| CHC1 | A | — | — | 0.14 | | 29 |
| | | | | 0.08 | | >33 |
| | | | | 0.13 | | >33 |
| CHC2 | A | Nap | Et | 0.12 | | >50 |
| CHC3 | A | Nap | Bn | 0.16 | | 44 |
| CHC4 | A | Nap | t-Bu | 2.36 | | >50 |
| CHC5 | G | — | — | 3 | 1.5 | >50 |
| | | | | 5 | | >50 |
| CHC6 | G | Nap | Bn | 0.08 | 0.06 | >50 |
| | | | | 0.032 | | >50 |
| | | | | 0.11 | | >50 |
| | | | | 0.13 | | >50 |
| | | | | 0.044 | | >50 |
| CHC7 | G | Nap | Et | 0.15 | | >50 |
| | | | | 0.2 | | >50 |
| | | | | 0.16 | | >50 |
| CHC8 | G | Nap | t-Bu | >50 | | >50 |
| CHC9 | G | Ph | Bn | 36 | 4.1 | >50 |
| CHC10 | G | Ph | Me | 0.87 | | >50 |
| | | | | 0.88 | | >50 |
| CHC11 | G | Nap | Me | 0.14 | | >50 |
| | | | | 0.063 | | >50 |

The data in Table I show that each of the compounds CHC6 and CHC7 embodying the present invention exhibits greater potency with respect to HCV than compound CHC5 which corresponds to the free nucleoside 9-linked guanine.

A comparison of the data in Table I with respect to each of compounds CHC6 and CHC9, and with respect to each of compounds CHC10 and CHC11, shows that the enhanced potency with respect to HCV is attributable to the presence in compounds CHC6 and CHC11, respectively, of Ar being 1-naphthyl.

Table II below sets out the structures of the presently exemplified compounds CHC1 to CHC11 in terms of formula I above, with in each case Z=H and Q=O.

TABLE II

| Compound | X | Y | T" | V | T | Ar | $R_1$ | $R_2$ | $R_3$ | $R_4$ |
|---|---|---|---|---|---|---|---|---|---|---|
| CHC1 | $NH_2$ | H | H | OH | H | — | — | — | — | — |
| CHC2 | $NH_2$ | H | H | OH | H | $C_{10}H_7$ | $CH_3$ | H | $CH_3CH_2$ | H |
| CHC3 | $NH_2$ | H | H | OH | H | $C_{10}H_7$ | $CH_3$ | H | $C_6H_5CH_2$ | H |
| CHC4 | $NH_2$ | H | H | OH | H | $C_{10}H_7$ | $CH_3$ | H | $t$-$C_4H_9$ | H |
| CHC5 | =O | $NH_2$ | H | OH | H | — | — | — | — | — |
| CHC6 | =O | $NH_2$ | H | OH | H | $C_{10}H_7$ | $CH_3$ | H | $C_6H_5CH_2$ | H |
| CHC7 | =O | $NH_2$ | H | OH | H | $C_{10}H_7$ | $CH_3$ | H | $CH_3CH_2$ | H |
| CHC8 | =O | $NH_2$ | H | OH | H | $C_{10}H_7$ | $CH_3$ | H | $t$-$C_4H_9$ | H |
| CHC9 | =O | $NH_2$ | H | OH | H | $C_6H_5$ | $CH_3$ | H | $C_6H_5CH_2$ | H |
| CHC10 | =O | $NH_2$ | H | OH | H | $C_6H_5$ | $CH_3$ | H | $CH_3$ | H |
| CHC11 | =O | $NH_2$ | H | OH | H | $C_{10}H_7$ | $CH_3$ | H | $CH_3$ | H |

Where Ar is $C_{10}H_7$, it is 1-naphthyl. Where X is $NH_2$, n is 0. Where X is =O, n is 1.

Each of compounds CHC1, CHC5, CHC9 and CHC10 is a comparative compound.

Compound CHC1 corresponds to the non-phosphoramidated, free nucleoside 9-linked adenine.

Compound CHC5 corresponds to the non-phosphoramidated, free nucleoside 9-linked guanine.

The invention claimed is:

1. A compound of formula I:

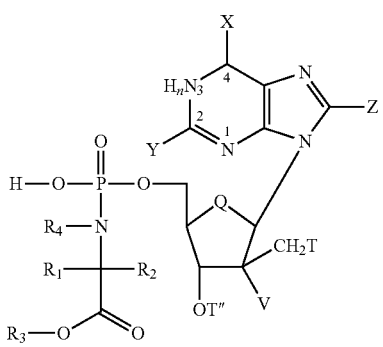

(I)

wherein:
Ar is naphthyl;
T is selected from the group consisting of hydrogen (H—), fluoro (F—), methyl (—$CH_3$) and ethyl (—$C_2H_5$);
V is selected from the group consisting of hydrogen (—H), fluoro (—F) and OT' where T' is selected from the group consisting of hydrogen (—H), and methyl (—$CH_3$);
T" is hydrogen (—H);
n is 0 or 1, wherein
when n is 1, X is =O, and
when n is 0, a double bond exists between position 3 and position 4 and X is selected from the group consisting of H, OH, F, Cl, Br, I, $C_{1-6}$alkyl and $NR_5R_6$, where each of $R_5$, and $R_6$ is independently selected from H and $C_{1-6}$ alkyl;
Z is selected from the group consisting of H, F, and Cl;
Y is selected from the group consisting of H, F, Cl, Br, $NH_2$ and $NR_5R_6$, where each of $R_5$ and $R_6$ is independently selected from H and $C_{1-6}$-alkyl;
Q is selected from the group consisting of O, and S;
each of $R_1$ and $R_2$ is independently selected from the group consisting of H, $C_{1-20}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy and $C_{5-20}$heterocyclyl, any of which is optionally substituted with a substituent selected from the group consisting of electron donating and electron withdrawing moieties;
each of $R_3$ and $R_4$ is independently selected from the group consisting of H, $C_{1-20}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy and $C_{5-20}$heterocyclyl, any of which is optionally substituted with a substituent selected from the group consisting of electron donating and electron withdrawing moieties;
with the proviso that —$R_1$ and $R_4$ are together defined as a —$(CH_2)_3$— alkylene chain;
and pharmaceutically acceptable salts thereof.

2. A compound according to claim 1 wherein Ar is unsubstituted 1-naphthyl.

3. A compound according to claim 1 wherein T is H, V is OH and T" is H.

4. A compound according to claim 1 wherein n is 1, X is =O and Y is $NH_2$.

5. A compound according to claim 4 wherein Z is H.

6. A compound according to claim 1 wherein n is 0, a double bond exists between position 3 and position 4, X is selected from the group consisting of $NH_2$, F, Cl and $NR_5R_6$ where one of $R_5$ and $R_6$ is H and the other of $R_5$ and $R_6$ is $C_{1-6}$-alkyl.

7. A compound according to claim 6 where X is $NH_2$, Y is H and Z is H.

8. A compound according to claim 1 wherein Q is O.

9. A compound according to claim 1 wherein $R_3$ is alkyl.

10. A compound according to claim 1 wherein $R_3$ is selected from the group consisting of methyl, ethyl, 2-propyl, n-propyl, cyclohexyl, 2-butyl and benzyl.

11. A compound according to claim 1 wherein $R_4$ is H.

12. A compound according to claim 1 wherein $R_1$ and $R_2$ are selected such that the moiety —N—$CR_1R_2$—COO— corresponds to the structure of a natural amino acid incorporated into the generic structure of formula I.

13. A compound according to claim 1 wherein each of $R_1$ and $R_2$ is independently selected from methyl (—$CH_3$) and H.

14. A compound according to claim 13 wherein one of $R_1$ and $R_2$ is methyl and one of $R_1$ and $R_2$ is H such that the C atom bearing $R_1$ and $R_2$ has chirality L as in natural alanine.

15. A compound according to claim 1 wherein Ar is unsubstituted.

16. A compound according to claim 1 comprising the diastereoisomer $R_P$, the diastereoisomer $S_P$ or a mixture of the diastereoisomers $R_P$ and $S_P$.

17. A compound selected from the group comprising:
β-2'-methyl-adenosine 5'-O-[α-naphthyl(ethoxy-L-alaninyl)]phosphate;
β-2'-methyl-adenosine 5'-O-[α-naphthyl(benzoxy-L-alaninyl)]phosphate;
β-2'-methyl-adenosine 5'-O-[α-naphthyl(tert-butoxy-L-alaninyl)]phosphate;
β-2'-methyl-guanosine 5'-O-[α-naphthyl(benzoxy-L-alaninyl)]phosphate;
β-2'-methyl-guanosine 5'-O-[α-naphthyl(ethoxy-L-alaninyl)]phosphate;
β-2'-methyl-guanosine 5'-O-[α-naphthyl(tert-butoxy-L-alaninyl)]phosphate;
and β-2'-methyl-guanosine 5'-O-[α-naphthyl(methoxy-L-alaninyl)]phosphate.

18. A pharmaceutical composition comprising a compound according to claim 1 in combination with a pharmaceutically acceptable carrier, diluent or excipient.

19. A method of treatment of a viral infection, comprising administering to a patient in need an effective dose of the compound according to claim 1.

20. The method according to claim 19 wherein the viral infection is hepatitis C virus.

21. A method of preparing a pharmaceutical composition comprising the step of physically mixing a compound according to claim 1 with a pharmaceutically acceptable excipient, carrier or diluent.

22. A process for the preparation of a compound of formula I as defined in claim 1, the process comprising reacting a compound of formula III:

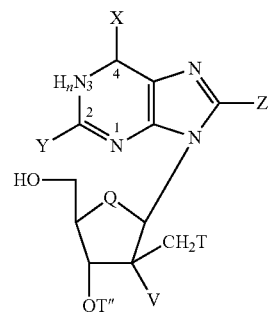

(III)

with a compound of formula IV:

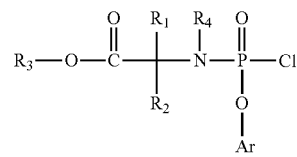

(IV)

where Ar, T, V, T", n, X, Y, Z, Q, $R_1$, $R_2$, $R_3$ and $R_4$, have the meanings as defined in claim 1.

* * * * *